(12) United States Patent
Esteller

(10) Patent No.: US 11,383,088 B2
(45) Date of Patent: Jul. 12, 2022

(54) METHOD AND APPARATUS FOR SELECTING NEUROMODULATION PARAMETERS USING ELECTROSPINOGRAM

(71) Applicant: Boston Scientific Neuromodulation Corporation, Valencia, CA (US)

(72) Inventor: Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 175 days.

(21) Appl. No.: 16/838,791

(22) Filed: Apr. 2, 2020

(65) Prior Publication Data

US 2020/0316382 A1  Oct. 8, 2020

Related U.S. Application Data

(60) Provisional application No. 62/829,186, filed on Apr. 4, 2019.

(51) Int. Cl.
*A61N 1/36* (2006.01)
*A61N 1/05* (2006.01)
*A61N 1/378* (2006.01)

(52) U.S. Cl.
CPC ....... *A61N 1/36139* (2013.01); *A61N 1/0534* (2013.01); *A61N 1/0551* (2013.01);
(Continued)

(58) Field of Classification Search
CPC ...... A61B 5/24; A61N 1/0534; A61N 1/0551; A61N 1/3605; A61N 1/36062;
(Continued)

(56) References Cited

U.S. PATENT DOCUMENTS 5,702,429 A 12/1997 King
2008/0004674 A1* 1/2008 King ............ A61N 1/0529
607/46

(Continued)

FOREIGN PATENT DOCUMENTS

CN 113966244 A 1/2022
WO WO-2020206152 A1 10/2020

OTHER PUBLICATIONS

"International Application Serial No. PCT/US2020/026431, International Preliminary Report on Patentability dated Oct. 14, 2021", 7 pgs.

(Continued)

*Primary Examiner* — George Manuel
(74) *Attorney, Agent, or Firm* — Schwegman Lundberg & Woessner, P.A.

(57) ABSTRACT

An example of a system for delivering neurostimulation energy may include a stimulation control circuit to control the delivery of the neurostimulation energy according to each of stimulation test patterns. The stimulation control circuit may include a sensing input configured to receive an electrospinogram (ESG) signal recording electrical activity from the spinal cord, a measurement circuit configured to determine one or more response parameters for each test pattern using the received ESG signal, and a selection circuit configured to select a neurostimulation therapy pattern from the stimulation test patterns based on the response parameter(s) and one or more selection criteria. The electrical activity includes responses to the delivered neurostimulation energy, and the response parameter(s) are each indicative of one or more characteristics of the responses. The selection may include selecting a type of stimulation waveform from multiple types of stimulation waveform in the stimulation test patterns.

20 Claims, 13 Drawing Sheets

(52) U.S. Cl.
CPC ....... *A61N 1/3615* (2013.01); *A61N 1/36071* (2013.01); *A61N 1/36178* (2013.01); *A61N 1/378* (2013.01)

(58) Field of Classification Search
CPC ............ A61N 1/36067; A61N 1/36071; A61N 1/36082; A61N 1/36139; A61N 1/36146; A61N 1/3615; A61N 1/36178; A61N 1/378
See application file for complete search history.

(56) References Cited

U.S. PATENT DOCUMENTS

| | | |
|---|---|---|
| 2014/0236257 A1 | 8/2014 | Parker et al. |
| 2016/0129272 A1 | 5/2016 | Hou et al. |
| 2018/0140843 A1 | 5/2018 | Kent et al. |
| 2018/0193651 A1 | 7/2018 | Annoni et al. |
| 2018/0214689 A1 | 8/2018 | Zhang et al. |
| 2018/0243564 A1 | 8/2018 | Stanslaski et al. |
| 2018/0369606 A1 | 12/2018 | Zhang et al. |
| 2018/0369607 A1 | 12/2018 | Zhang et al. |

OTHER PUBLICATIONS

"International Application Serial No. PCT/US2020/026431, International Search Report dated Jul. 13, 2020", 5 pgs.
"International Application Serial No. PCT/US2020/026431, Written Opinion dated Jul. 13, 2020", 5 pgs.

* cited by examiner

METHOD AND APPARATUS FOR SELECTING NEUROMODULATION PARAMETERS USING ELECTROSPINOGRAM

CLAIM OF PRIORITY

This application claims the benefit of priority under 35 U.S.C. § 119(e) of U.S. Provisional Patent Application Ser. No. 62/829,186, filed on Apr. 4, 2019, which is herein incorporated by reference in its entirety.

TECHNICAL FIELD

This document relates generally to neuromodulation and more particularly to a method and system for automatically selecting stimulation parameters for neuromodulation using electrospinogram (ESG).

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical pulses. The delivery is controlled using stimulation parameters that specify spatial (where to stimulate), temporal (when to stimulate), and informational (patterns of pulses directing the nervous system to respond as desired) aspects of a pattern of the electrical pulses. Efficacy and efficiency of certain neurostimulation therapies can be improved, and their side-effects can be reduced, by determining these stimulation parameters based on a patient's conditions and therapeutic objectives. While modern electronics can accommodate the need for generating sophisticated pulse patterns, the capability of a neurostimulation system depends on how stimulation parameters defining such a pulse pattern can be determined and adjusted for the patient to ensure efficacy and efficiency of a therapy using neurostimulation when applied to the patient.

SUMMARY

An example (e.g., "Example 1") of a system for delivering neurostimulation energy through a plurality of electrodes to a patient having a spinal cord may include a stimulation control circuit that may be configured to control the delivery of the neurostimulation energy according to each test pattern of a plurality of neurostimulation test patterns. The stimulation control circuit may include a sensing input, a measurement circuit, and a selection circuit. The sensing input may be configured to receive an electrospinogram (ESG) signal recording electrical activity from the spinal cord. The electrical activity includes responses to the delivered neurostimulation energy. The measurement circuit may be configured to determine one or more response parameters for each test pattern of the plurality of neurostimulation test patterns using the received ESG signal. The one or more response parameters are each indicative of one or more characteristics of the responses to the delivered neurostimulation energy. The selection circuit may be configured to select a neurostimulation therapy pattern from the plurality of stimulation test patterns based on the one or more response parameters and one or more selection criteria. The selection may include selecting a type of stimulation waveform from multiple types of stimulation waveform in the plurality of stimulation test patterns.

In Example 2, the subject matter of Example 1 may optionally be configured such that the selection circuit is configured to select the neurostimulation therapy pattern from the plurality of stimulation test patterns periodically or in response to a need for a selection update being identified.

In Example 3, the subject matter of any one or any combination of Examples 1 and 2 may optionally be configured such that the measurement circuit is configured to determine one or more neural response parameters of the one or more response parameters and the selection circuit is configured to select the neurostimulation therapy pattern from the plurality of stimulation test patterns based on the one or more neural response parameters and the one or more selection criteria. The one or more neural response parameters are each indicative of one or more characteristics of evoked responses each being a neural response evoked by the delivered neurostimulation energy, In Example 4, the subject matter of any one or any combination of Examples 1 to 3 may optionally be configured such that the neurostimulation test patterns are each defined by one or more waveforms each specifying a temporal pattern of the neuromodulation energy including the type of stimulation waveform, and the multiple types of stimulation waveform include active recharge waveforms.

In Example 5, the subject matter of any one or any combination of Examples 1 to 4 may optionally be configured such that the neurostimulation patterns are each defined by one or more fields each specifying a spatial distribution of the neurostimulation energy across the plurality of electrodes.

In Example 6, the subject matter of any one or any combination of Examples 3 to 5 may optionally be configured such that the measurement circuit is further configured to determine values of the one or more neural response parameters each corresponding to a test pattern of the plurality of neurostimulation test patterns, and the selection circuit is further configured to select the neurostimulation therapy pattern by selecting the test pattern corresponding to a value of the determined values identified according to the one or more selection criteria.

In Example 7, the subject matter of Example 6 may optionally be configured such that the selection circuit is configured to select the neurostimulation therapy pattern by selecting the test pattern corresponding to a maximum evoked response identified from the evoked responses corresponding to the plurality of neurostimulation test patterns.

In Example 8, the subject matter of Example 7 may optionally be configured such that the measurement circuit is further configured to determine a curve area of the one or more neural response parameters. The curve area is an area between the ESG signal and a baseline over a specified time interval.

In Example 9, the subject matter of Example 7 may optionally be configured such that the measurement circuit is further configured to determine a curve length of the one or more neural response parameters. The curve length is a duration of the evoked responses over a specified time interval.

In Example 10, the subject matter of Example 7 may optionally be configured such that the measurement circuit is further configured to determine a peak-to-peak amplitude of the one or more neural response parameters. The peak-to-peak amplitude is a difference between amplitudes of two specified-type peaks in the ESG signal.

In Example 11, the subject matter of Example 7 may optionally be configured such that the measurement circuit is further configured to produce a derivative of the received ESG signal and further configured to determine one or more additional neural response parameters using the produced derivative of the received ESG signal. The one or more additional neural response parameters are each indicative of one or more further characteristics of the evoked responses.

In Example 12, the subject matter of any one or any combination of Examples 6 to 11 may optionally be configured such that the selection circuit is configured to select the neurostimulation therapy pattern by selecting the test pattern corresponding to a maximum pain-paresthesia overlap identified from the evoked responses corresponding to the plurality of neurostimulation test patterns.

In Example 13, the subject matter of Example 12 may optionally be configured such that the selection circuit is configured to compare the received ESG signals to previously recorded ESG signals to identify the test pattern based on similarity to portions of the previously recorded ESG signals corresponding to a maximum pain-paresthesia overlap.

In Example 14, the subject matter of any one or any combination of Examples 1 to 13 may optionally be configured such that the stimulation control circuit is further configured to control the delivery of the neurostimulation energy according to the selected neurostimulation therapy pattern and further includes a adjustment circuit configured to adjust one or more stimulation parameters of the selected neurostimulation therapy pattern based on the one or more neural response parameters measured after the delivery of the neurostimulation energy according to the neurostimulation therapy pattern has started.

In Example 15, the subject matter of Example 14 may optionally be configured such that the adjustment circuit is further configured to adjust the one or more stimulation parameters of the selected neurostimulation therapy pattern so that a value of each of the adjusted one or more stimulation parameters is maintained within a specified range.

An example (e.g., "Example 16") of a method for delivering neurostimulation energy through a plurality of electrodes to a patient having a spinal cord is also provided. The method may include controlling delivery of the neurostimulation energy according to each test pattern of a plurality of neurostimulation test patterns, receiving an electrospinogram (ESG) being a recording of electrical activity from the spinal cord, determining one or more response parameters for each test pattern of the plurality of neurostimulation test patterns using the received ESG signal, and selecting a neurostimulation therapy pattern from the plurality of stimulation test patterns based on the one or more response parameters and one or more selection criteria. The electrical activity includes responses to the delivered neurostimulation energy. The one or more response parameters are each indicative of one or more characteristics of the responses to the delivered neurostimulation energy. The selection may include selecting a type of stimulation waveform from multiple types of stimulation waveform in the plurality of stimulation test patterns.

In Example 17, the subject matter of determining the one or more response parameters as found in Example 16 may optionally include determining one or more neural response parameters each indicative of one or more characteristics of evoked responses each being a neural response evoked by the delivered neurostimulation energy, and the subject matter of selecting the neurostimulation therapy pattern as found in Example 16 may optionally include selecting the neurostimulation therapy pattern from the plurality of stimulation test patterns based on the one or more neural response parameters and the one or more selection criteria.

In Example 18, the subject matter of selecting the neurostimulation therapy pattern as found in any one or any combination of Examples 16 and 17 may optionally include selecting a waveform specifying a temporal pattern of the neuromodulation energy including the type of stimulation waveform, and the multiple types of stimulation waveform include active recharge waveforms.

In Example 19, the subject matter of selecting the neurostimulation therapy pattern as found in any one or any combination of Examples 16 to 18 may optionally include selecting a field specifying a spatial distribution of the neurostimulation energy across the plurality of electrodes.

In Example 20, the subject matter of determining the one or more neural response parameters as found in any one or any combination of Examples 17-19 may optionally include determining values of the one or more neural response parameters each corresponding to a test pattern of the plurality of neurostimulation test patterns, and the subject matter of selecting the neurostimulation therapy pattern as found in any one or any combination of Examples 17-19 may optionally include selecting the test pattern corresponding to a value of the determined values that indicates a maximum evoked response of the evoked responses corresponding to the plurality of neurostimulation test patterns.

In Example 21, the subject matter of determining the one or more neural response parameters as found in any one or any combination of Examples 17 to 20 may optionally include determining at least one of a curve area being an area between the ESG signal and a baseline over a specified time interval, a curve length being a duration of the evoked responses over a specified time interval, a peak-to-peak amplitude being a difference between amplitudes of two specified-type peaks in the ESG signal, or one or more neural response parameters measured from a derivative of the received ESG signal.

In Example 22, the subject matter of selecting the neurostimulation therapy pattern as found in any one or any combination of Examples 17 to 21 may optionally include selecting the test pattern corresponding to a maximum pain-paresthesia overlap identified from the evoked responses corresponding to the plurality of neurostimulation test patterns.

In Example 23, the subject matter of any one or any combination of Examples 17 to 22 may optionally include controlling the delivery of the neurostimulation energy according to the selected neurostimulation therapy pattern and adjusting one or more stimulation parameters of the selected neurostimulation therapy pattern based on the one or more neural response parameters measured after the delivery of the neurostimulation energy according to the neurostimulation therapy pattern has started so that a value of each of the adjusted one or more stimulation parameters is maintained within a specified range during the delivery of the neurostimulation energy according to the neurostimulation therapy pattern.

An example (e.g., "Example 24") of a non-transitory computer-readable storage medium including instructions, which when executed by a system, cause the system to perform a method for delivering neurostimulation energy through a plurality of electrodes to a patient having a spinal cord is also provided. The method may include controlling delivery of the neurostimulation energy according to each test pattern of a plurality of neurostimulation test patterns, receiving an electrospinogram (ESG) being a recording of electrical activity from the spinal cord, determining one or more response parameters for each test pattern of the plurality of neurostimulation test patterns using the received ESG signal, and selecting a neurostimulation therapy pattern from the plurality of stimulation test patterns based on the one or more response parameters and one or more selection criteria. The electrical activity includes responses to the delivered neurostimulation energy. The one or more response parameters are each indicative of one or more characteristics of the responses to the delivered neurostimulation energy. The selection may include selecting a type of stimulation waveform from multiple types of stimulation waveform in the plurality of stimulation test patterns.

In Example 25, the subject matter of Example 24 may optionally be configured such that determining the one or more response parameters includes determining one or more neural response parameters each indicative of one or more characteristics of evoked responses each being a neural response evoked by the delivered neurostimulation energy, and selecting the neurostimulation therapy pattern includes selecting the neurostimulation therapy pattern from the plurality of stimulation test patterns based on the one or more neural response parameters and the one or more selection criteria.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
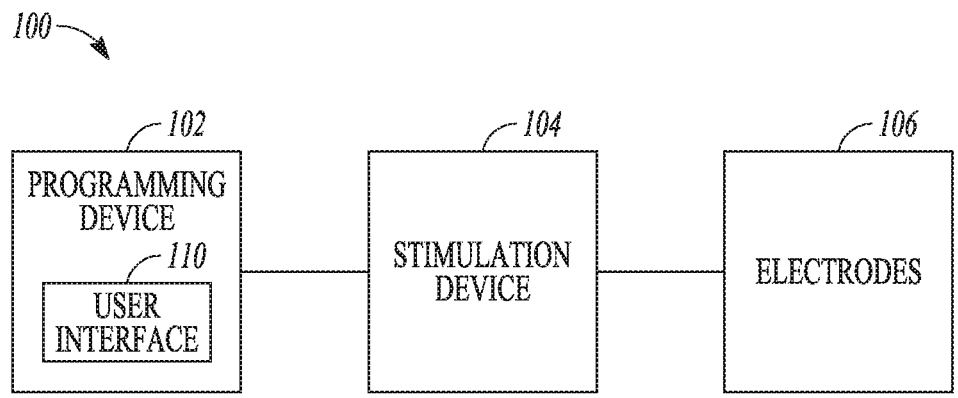
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that can use information extracted from a patient's electrospinogram (ESG) to control delivery of neurostimulation to the patient. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. While delivery of SCS using an implantable device is discussed as a specific example, the present subject matter can also be applied to program stimulation devices for delivering various types of neuromodulation therapies.

ESG is a recording of electrical activity from the spinal cord. Many nerve cells produce low-level electrical signals, called action potentials, that form electrical activity patterns and in many instances can have an additive effect producing a magnified neural response. An example is the evoked compound action potential (ECAP), which is evoked by a stimulation such as a neurostimulation pulse and results from many neural cells firing simultaneously or close in time. An ESG signal also include neural components having a random appearance and representing activities of many different types of cells of the patient's nervous system that spontaneously fire over the time. The ESG signal further includes non-neural components representing various physical movements of the patient, such as movements associated with cardiac activities, respiratory activities, and skeletomuscular activities.

An ESG signal can be sensed non-invasively using surface electrodes attached to the patient's skin. This surface sensing usually requires an amplifier with high gain and high signal-to-noise ratio (SNR). An ESG signal can also be sensed invasively using electrodes incorporated onto one or more percutaneous or implantable leads. In one example, the ESG signal is sensed epidurally using epidural electrodes placed adjacent or over the dura, which is a membrane structure surrounding the spinal cord and the cerebral cortex of the patient. In another example, the ESG signal is sensed intradurally using a lead that penetrates the dura such that the electrodes can be placed subdurally within the spinal cord.

Findings from recent clinical studies suggest fast acting pain relief can be achieved by using SCS with active recharge waveforms with intensity just below the threshold for paresthesia resulting from dorsal column activation. ESG signals can be sensed from the patient to indicate characteristics (e.g., amplitude and shape) of the patient's dorsal column response to the stimulation, and therefore can be used for evaluation of stimulation parameters (e.g., waveforms and tissue sites of stimulation) to select a suitable pattern of stimulation. It has been observed that the neural responses evoked by SCS with active recharge waveforms exhibit an increasing magnitude and a changing shape as the stimulation increases and changes, respectively, with stimulation amplitude, stimulation pulse width, and/or closeness of stimulation site to the spinal cord. Dorsal column fibers of different diameters are known to produce a neural response after different delays, with fibers of smaller diameters associated with greater delays. The ECAP detectable from the ESG is a result of additive effect of the multiple action potentials produced by different axons of different diameters firing with different delays. The present system can use ECAPs as presented in ESG to indicate a desirable response of neurostimulation and evaluate various neurostimulation patterns for selecting a suitable pattern for a patient to control delivery of a therapy to the patient. In this document, a "patient" includes a person receiving treatment delivered using a neurostimulation system according to the present subject matter, a "user" includes a physician or other caregiver who treats the patient using the neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for SCS applications. Such SCS configuration includes various features that may simplify the task of the user in programming stimulation device 104 for delivering SCS to the patient, such as the features discussed in this document.

Figure 2:
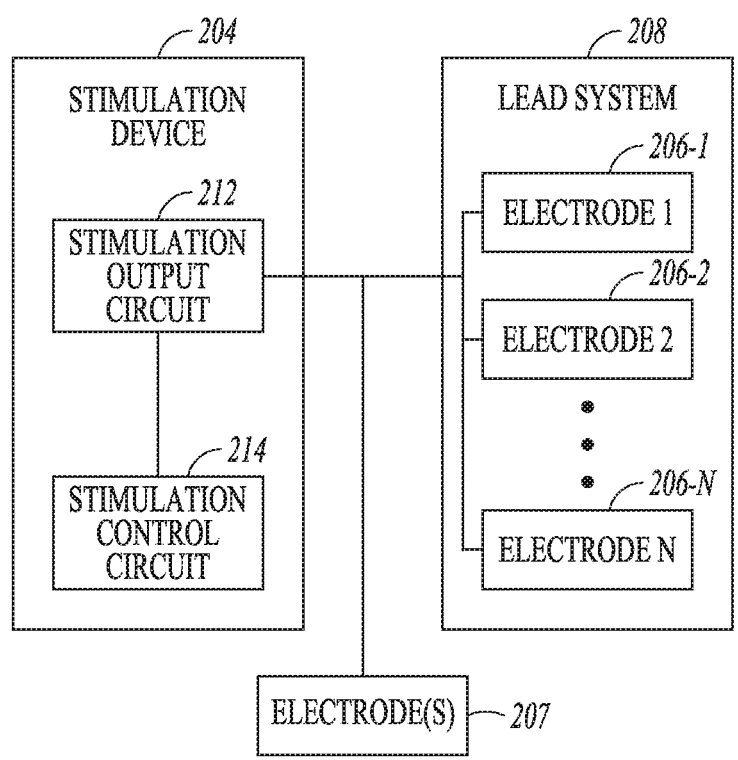
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
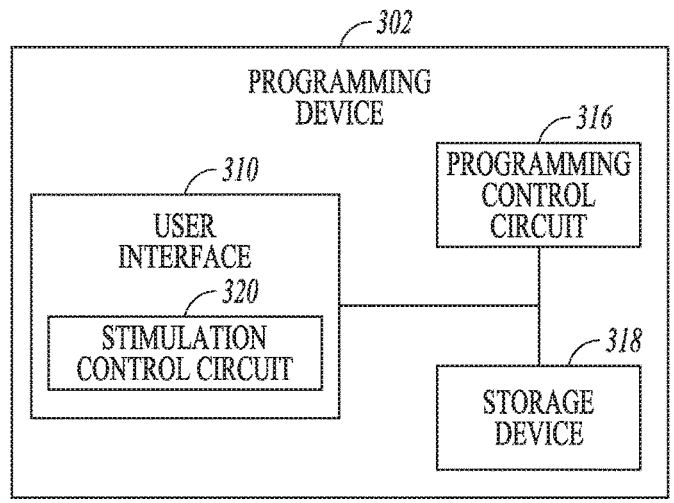
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
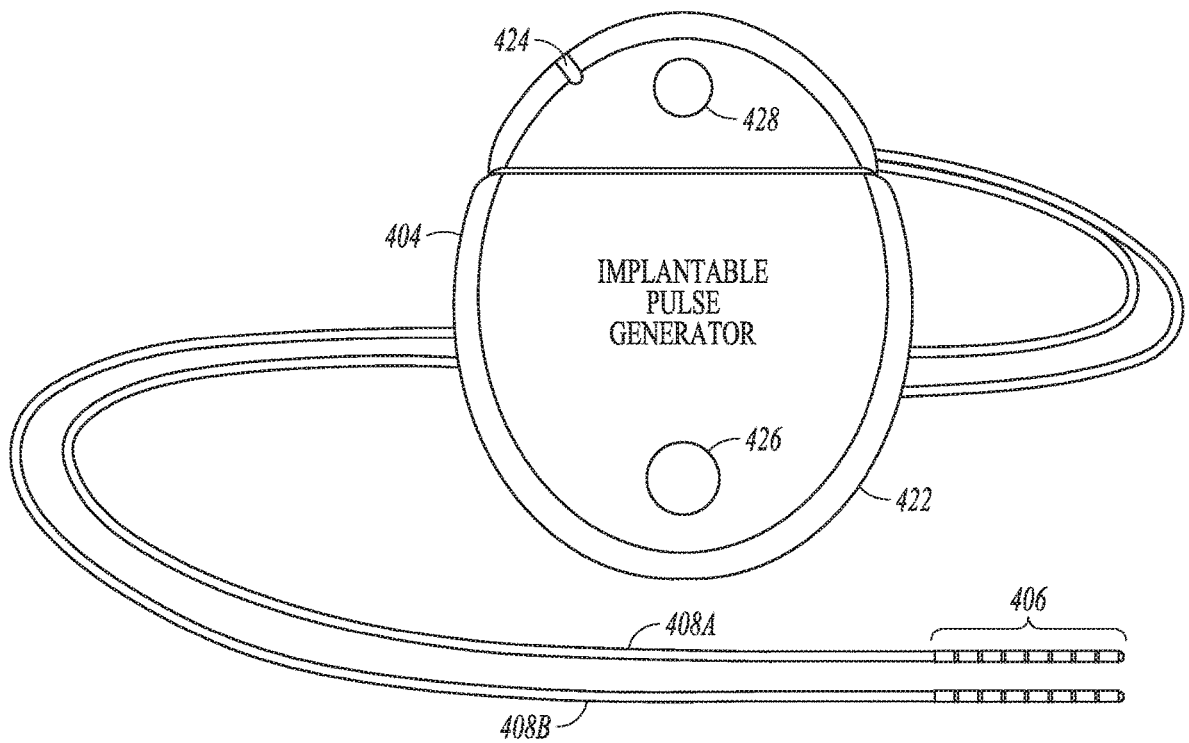
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to a nerve cell target included in the subject's spinal cord.

Figure 5:
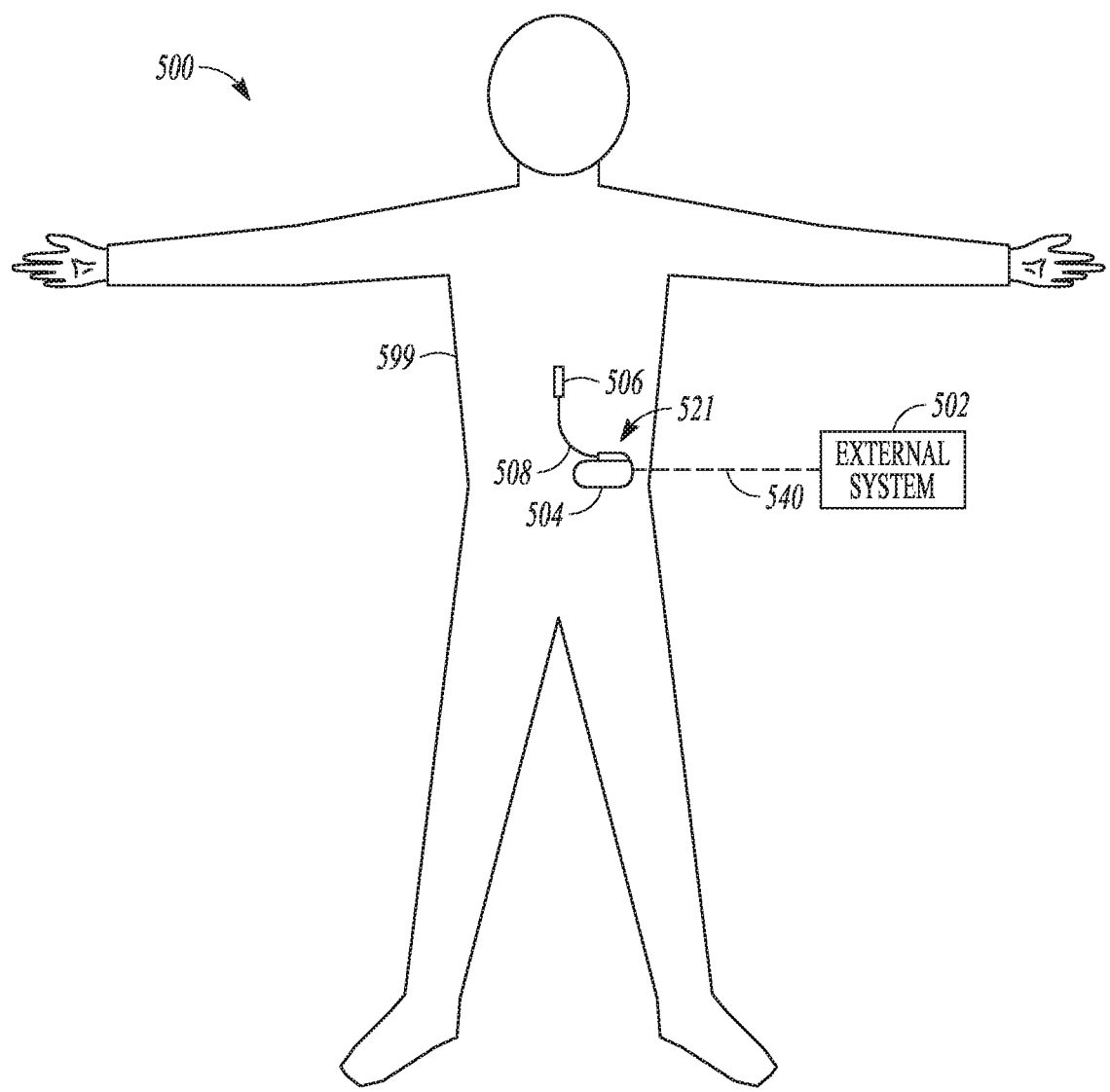
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
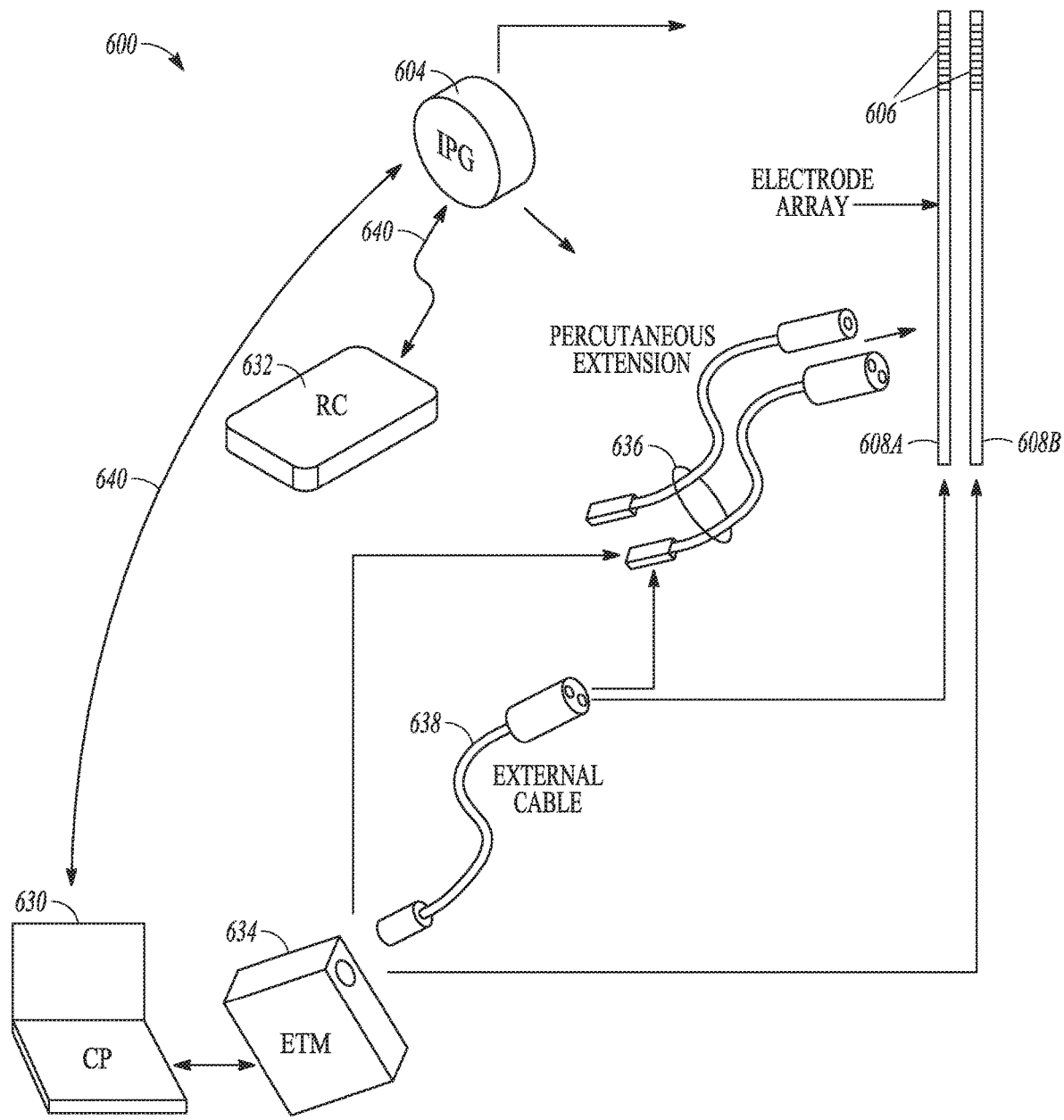
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically coupled to leads 608A and 608B directly or through percutaneous extension leads 636. ETM 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as IPG 604 to deliver neurostimulation energy according to specified modulation parameters as discussed above. ETM 634 is an external device that is typically used as a preliminary stimulator after leads 408A and 408B have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630, CP 630 may communicate with ETM 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pukes or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
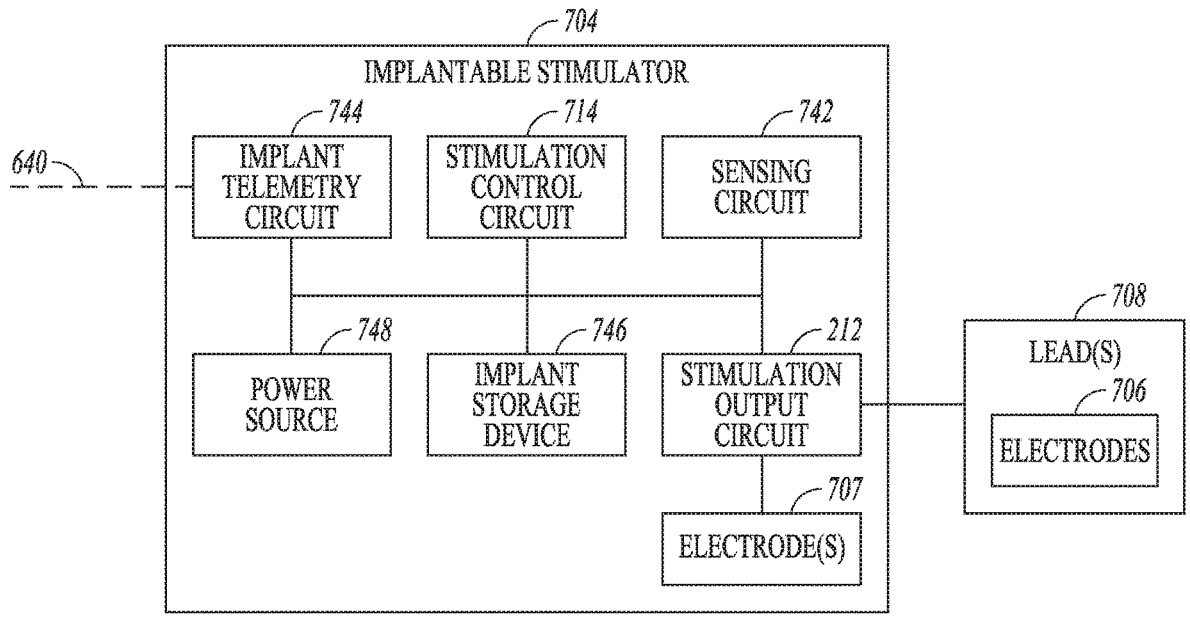
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that provides the stimulator with a sensing capability, stimulation output circuit 212, a stimulation control circuit 714, an implant storage device 746, an implant telemetry circuit 744, a power source 748, and one or more electrodes 707. Sensing circuit 742 can one or more physiological signals for purposes of patient monitoring and/or feedback control of the neurostimulation. In various embodiments, sensing circuit 742 can sense one or more ESG signals using electrodes placed over or under the dura of the spinal cord, such as electrodes 706 (which can include epidural and/or intradural electrodes). In addition to one or more ESG signals, examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
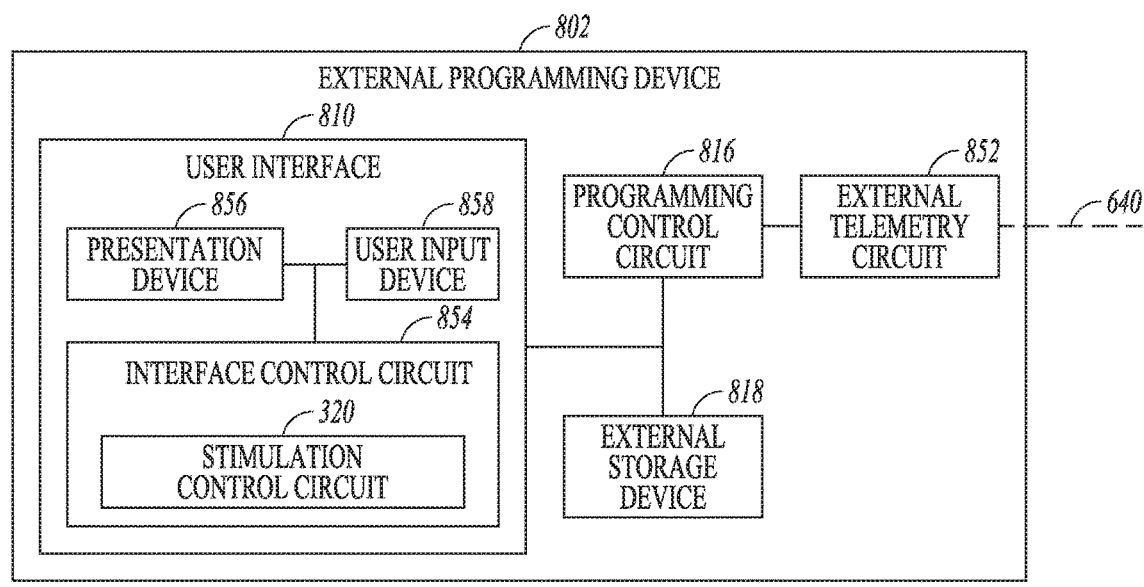
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). This can allow for patient mobility during programming and assessment when needed. For example, wireless communication link 640 can include at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
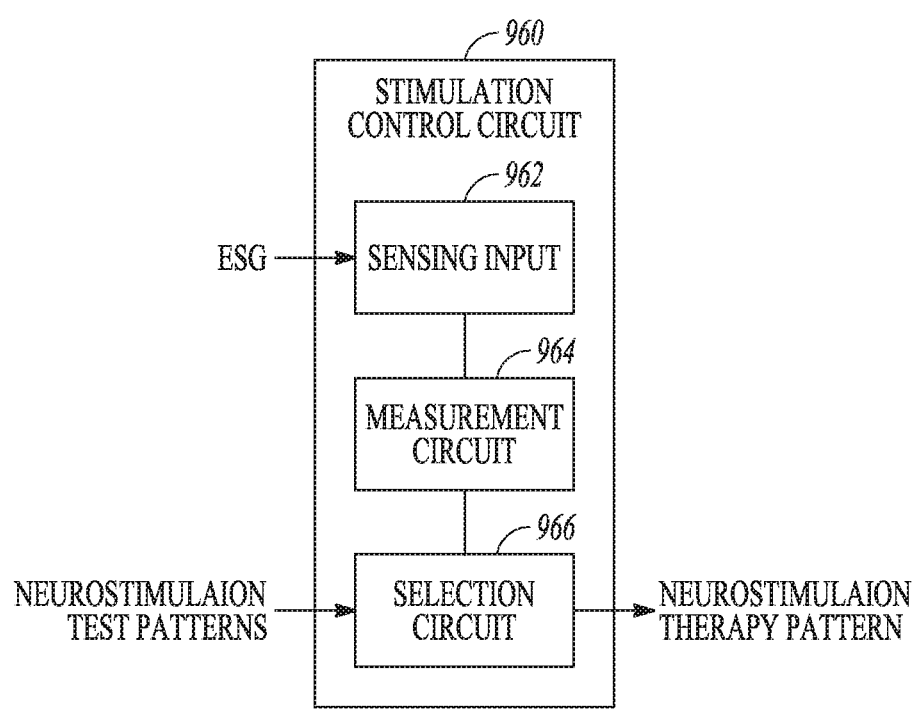
FIG. 9 illustrates an embodiment of a stimulation control circuit for selecting a neurostimulation pattern using electrospinogram (ESG).

FIG. 9 illustrates an embodiment of a stimulation control circuit 960 for selecting a neurostimulation pattern using ESG. In this document, a "neurostimulation pattern" can refer to a set of stimulation parameters for controlling the delivery of the neurostimulation energy for a neurostimulation program, a neurostimulation therapy session, or any other unit of delivery of neurostimulation. A neurostimulation pattern can be defined by a neurostimulation program (including stimulation parameters).

Stimulation control circuit 960 can control the delivery of the neurostimulation energy according to each test pattern of a plurality of neurostimulation test patterns and can include a sensing input 962, a measurement circuit 964, and a selection circuit 966. Sensing input 962 can receive an ESG signal indicative of responses to the delivered neurostimulation energy. Measurement circuit 964 can determine one or more response parameters for each test pattern of the plurality of neurostimulation test patterns using the received ESG signal. The one or more response parameters can each indicate one or more characteristics of the responses to the delivered neurostimulation energy. Selection circuit 966 can select a neurostimulation therapy pattern from the plurality of stimulation test patterns based on the one or more response parameters and one or more selection criteria. In this document, a "neurostimulation test pattern" can refer to a neurostimulation pattern developed for evaluation purposes, such as for evaluating its efficacy in a patient by delivering neurostimulation energy to the patient according to the neurostimulation test pattern, and a "neurostimulation therapy pattern" can refer to a neurostimulation pattern determined for therapeutic purposes, such as for treating the patient by delivering neurostimulation energy to the patient according to the determined neurostimulation therapy pattern.

The selection performed by selection circuit 966 can include selecting a type of stimulation waveform from multiple types of stimulation waveform in the plurality of stimulation test patterns. The type of stimulation waveform including example are discussed below with reference to FIGS. 12A-D.

The response to the delivered neurostimulation energy include neural response evoked by the delivered neurostimulation energy, called evoked responses. The one or more response parameters can include one or more neural response parameters each indicative of one or more characteristics of the evoked responses. Measurement circuit 964 can determine the one or more neural response parameters for each test pattern of the plurality of neurostimulation test patterns using the received ESG signal. Selection circuit 966 can select the neurostimulation therapy pattern from the plurality of stimulation test patterns based on the one or more neural response parameters and the one or more selection criteria.

Figure 10:
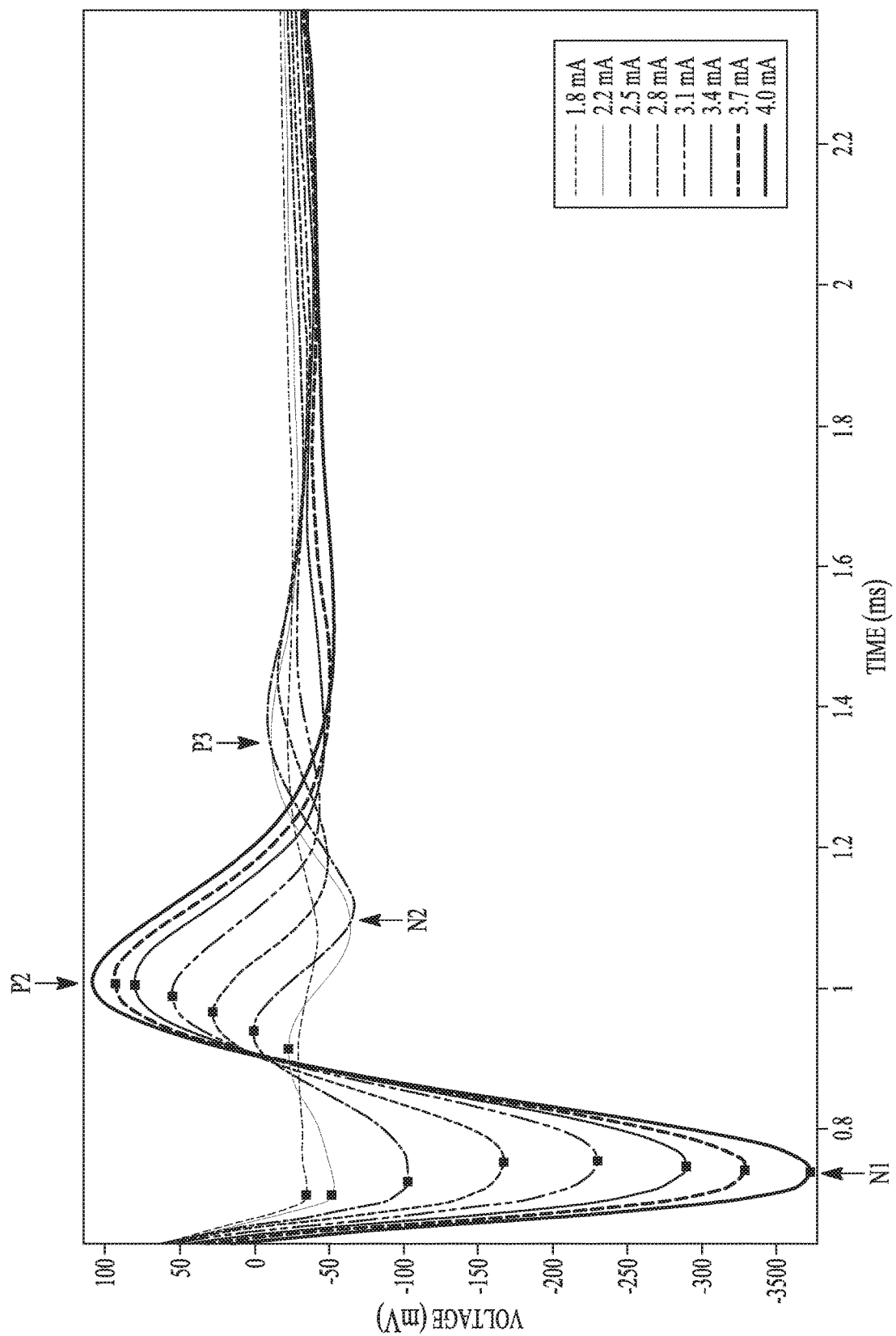
FIG. 10 is a graph showing an example of neural responses evoked by neurostimulation pulses as seen on ESG.

FIG. 10 is a graph showing an example of neural responses evoked by neurostimulation pulses as seen on ESG. The neural responses as shown are dorsal column responses seen on an ESG signal and resulting from stimulation with electrical pulses having various amplitudes. A stronger dorsal column response resulting from stimulation with a higher pulse amplitude is characterized by a greater magnitude and different shape including, for example:

a greater N1-to-P2 amplitude, where N1 is the first negative peak in an evoked response that is correlated to the response of faster fibers such as Aβ fibers and myelinated fibers, and P2 is the second positive peak in the evoked response that is correlated with response of slower fibers;

a greater N1 to P2 curve length;

a greater overall ESG curve length;

a greater ESG area under the curve (area between the ESG and the zero-volt baseline);

a greater P2 peak delay, which is the time interval between the neurostimulation pulse and the P2 of the evoked response and is indicative of recruitment of slower (smaller diameter) fibers; and presence of N2 and P3, wherein N2 is the second negative peak in the evoked response, and P3 is the third positive peak in the evoked response, which are correlated with responses of even slower fibers (e.g., Aδ fibers).

The one or more neural response parameters used for selecting the neurostimulation therapy pattern from the plurality of stimulation test patterns can be derived from such characteristics of the evoked responses as seen on the ESG signal. In various embodiments, the one or more neural response parameters can be measured from the ESG signal and/or a derivative of the ESG signal.

In one embodiment, a criterion for selecting the neurostimulation therapy pattern from the plurality of stimulation test patterns includes selecting the test pattern corresponding to a maximum evoked response identified from the evoked responses corresponding to the plurality of neurostimulation test patterns. An evoked response can include the response evoked by a stimulus such as a stimulation pulse or any unit of stimulation considered to be a single stimulus. Examples of the one or more neural response parameters used with this selection criterion include:

area under the curve (the area between the ESG signal and a baseline for an evoked response or another specified period, also referred to curve area in this document), which can be determined using:

$$A = \sum_{n=1}^{N} |y(n)|,$$

where A is the area under the curve, n is the time index, y is the data time series, and N is the index of the last data sample in the time series;

curve length (duration of an evoked response measured from the ESG signal which can be determined using:

$$CL = \sum_{n=2}^{N-1} |y(n) - y(n-1)|,$$

where CL is the curve length;

N1-to-P2 amplitude (the difference between amplitudes of N1 and P2); and/or curve length of ESG derivative (duration of an evoked response measures from a derivative of the ESG signal).

In another embodiment, a criterion for selecting the neurostimulation therapy pattern from the plurality of stimulation test patterns includes selecting the test pattern that maximizes the overlap between the body areas with pain (dermatomes with pain) and the dermatomes where the patient feels the paresthesia sensation produced by the stimulation pattern. The test pattern achieving this maximum pain-paresthesia overlap is identified from the evoked responses corresponding to the plurality of neurostimulation test patterns. The selection can also be done with patient feedback and by comparing to previously recorded ESG signals and identify the test pattern based on similarity to portions of the previously recorded ESG signals corresponding to a maximum pain-paresthesia overlap.

In various embodiments, these two criteria can be used individually, in combination with each other, or in combination with one or more other criteria, or one or more other criteria can be used, for the selection of the neurostimulation therapy pattern from the plurality of stimulation test patterns. In various embodiments, the plurality of neurostimulation test patterns allow for evaluation of various waveforms and/or fields (stimulation sites) to select the neurostimulation therapy pattern including a suitable or optimal waveform, field, or combination of waveform and field according to the one or more selection criteria. In various embodiments, the evaluation process can be done automatically. For example, stimulation control circuit 960 can control the delivery of the neurostimulation energy by automatically sequencing through the plurality of neurostimulation test patterns. In various embodiments, the evaluation process can be done manually. For example, stimulation control circuit 960 can control the delivery of the neurostimulation energy by allowing the user to manually enter and/or start each text pattern of the plurality of neurostimulation test patterns.

Figure 11:
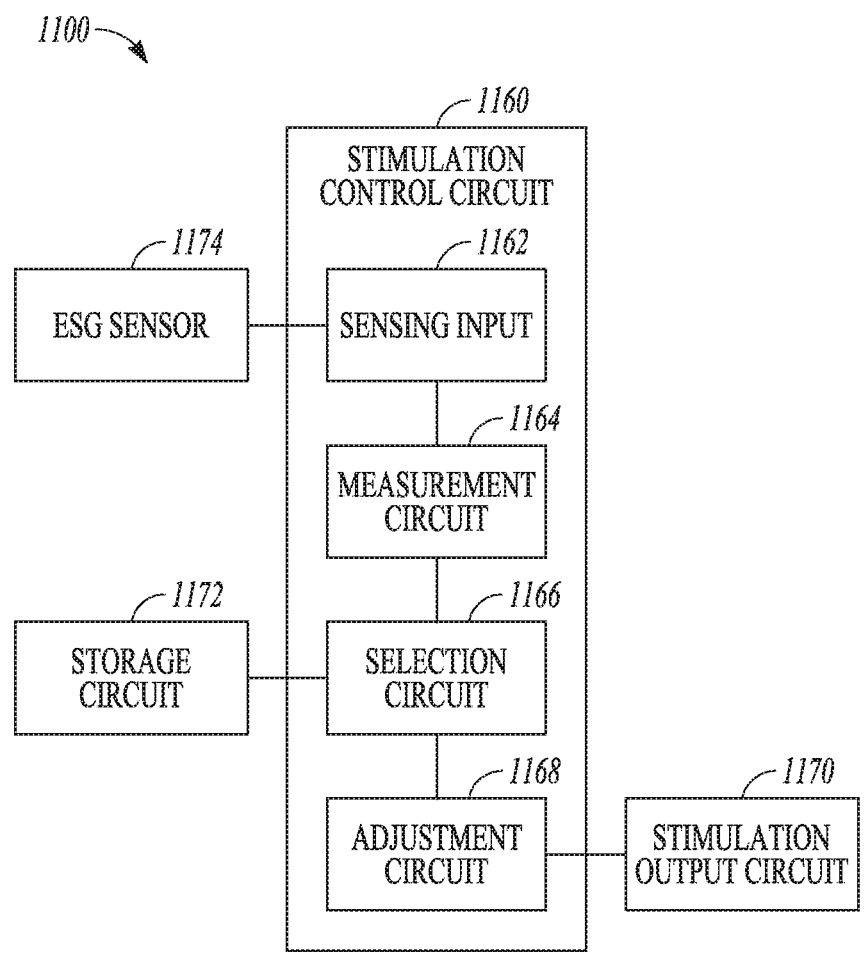
FIG. 11 illustrates an embodiment of a system for delivering neurostimulation, including a stimulation control circuit for selecting a neurostimulation pattern using ESG.

FIG. 11 illustrates an embodiment of a system 1100 for delivering neurostimulation including a stimulation control circuit 1160 for selecting a neurostimulation pattern using ESG. System 1100 can be implemented in a neurostimulation system such as system 100, 500, and 600 and used for selecting a neurostimulation pattern to be in that system for controlling delivery of neurostimulation energy.

System 1100 can include a stimulation output circuit 1170 to deliver neurostimulation energy through a plurality of electrodes. An example of stimulation output circuit 1170 as implemented in the neurostimulation system includes stimulation output circuit 212. Examples for the plurality of electrodes include electrodes 106, 206, 406, 506, 606, and 706. Stimulation output circuit 1170 can generate one or more stimulation waveforms including one or more active recharge waveforms and/or one or more passive recharge waveforms.

System 1100 can include an ESG sensor 1174 to sense at least one ESG signal. ESG sensor 1174 as implemented in the neurostimulation system can include electrodes that can be positioned to sense ESG and a sensing circuit to produce the ESG signal for use by stimulation control circuit 1160. The electrodes can be incorporated into a lead system of the neurostimulation system, such as lead system 208, 408, 508, 608, and 708, and the sensing circuit can be included in sensing circuit 742.

Stimulation control circuit 1160 can represent an example of stimulation control circuit 960 and can control the delivery of the neurostimulation energy according to a test pattern selected from a plurality of neurostimulation test patterns. System 1100 can include a storage circuit 1172 to store the plurality of neurostimulation test patterns. In one embodiment, stimulation control circuit 1160 and storage circuit 1172 as implemented in the neurostimulation system include a control circuit and a storage device of a stimulation device, such as stimulation control circuit 214 of stimulation device 204 or stimulation control circuit 714 of implantable stimulator 704, and implant storage device 746 of implantable stimulator 704. In another embodiment, stimulation control circuit 1160 and storage circuit 1172 as implemented in the neurostimulation system include a control circuit and a storage device of a programming device, such as stimulation control circuit 320 of programming device 302 or external programming device 802, and external storage device 818 of external programming device 802.

Each neurostimulation pattern (test or therapy pattern) is defined by stimulation parameters (e.g., by a neurostimulation program including the stimulation parameters). The stimulation parameters can include one or more waveforms each specifying a temporal pattern of the neuromodulation energy. The one or more waveform can include one or more passive recharge waveform and/or one or more active recharge waveforms. FIG. 12A-I each illustrate an example of a type of stimulation waveform. Each illustrated stimulation waveform includes stimulation pulses each including a stimulation (charge injection) phase, a recharge (charge recovery) phase, and an interphase delay (which can be programmed to zero, i.e., no interphase delay). The type of a stimulation waveform can be defined, for example, by one or more of:

active or passive recharge (i.e., whether the recharge phase is actively or passively driven);

the shape of the stimulation and/or recharge phases (e.g., rectangular, sinusoidal, or triangular); and polarity of the stimulation phase (e.g., cathodic, anodic, or alternating).

Figure 12A:
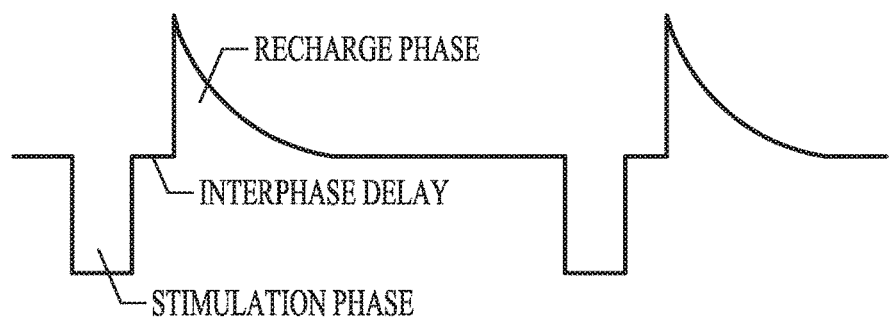
FIG. 12A-I each illustrate an example of a stimulation waveform.
Figure 12B:
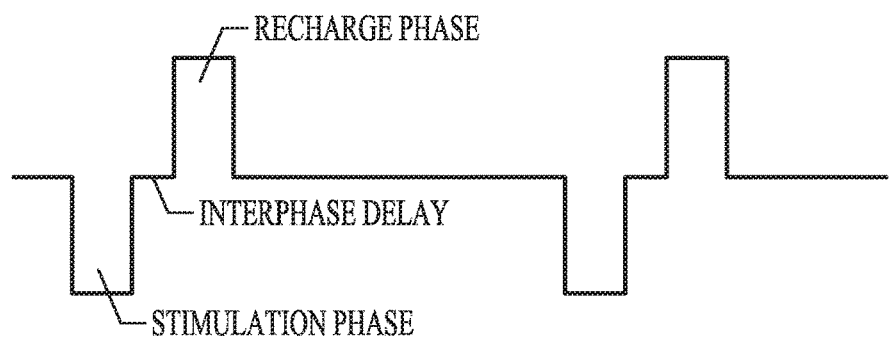
Figure 12C:
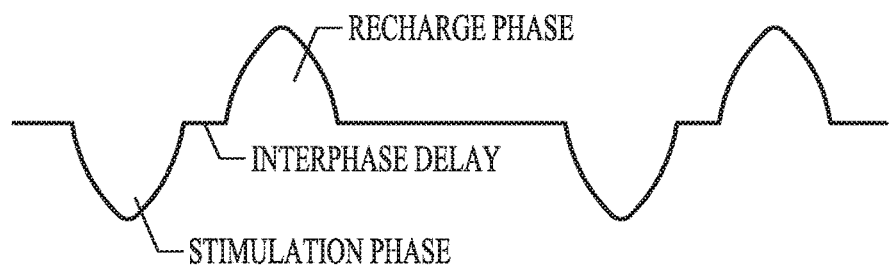
Figure 12D:
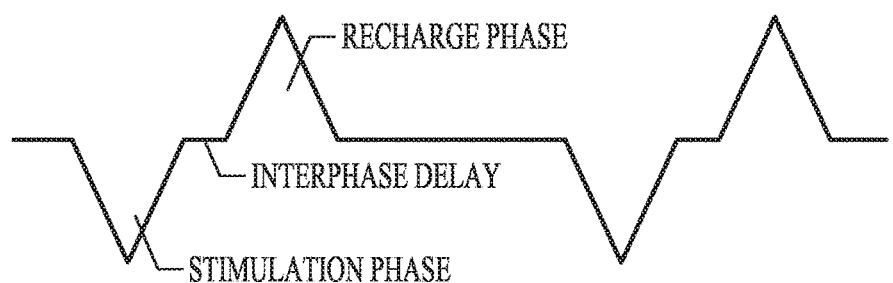
Figure 12E:
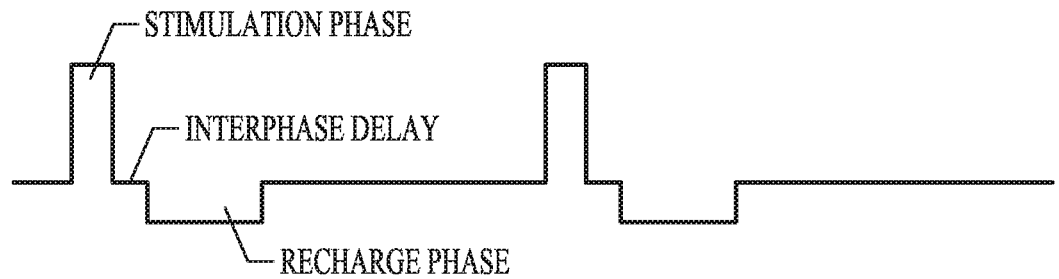
Figure 12F:
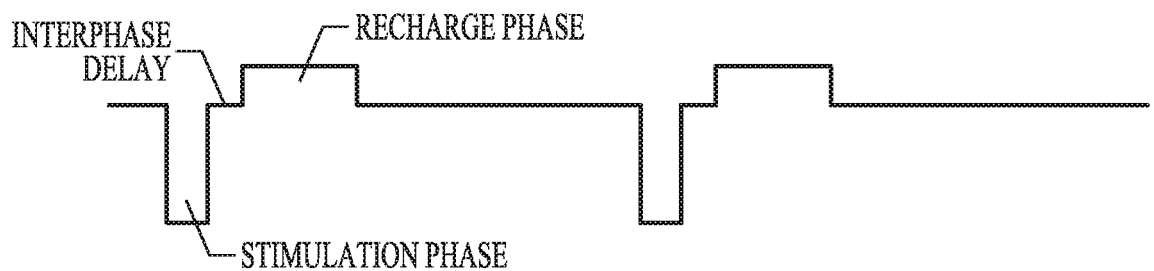
Figure 12G:
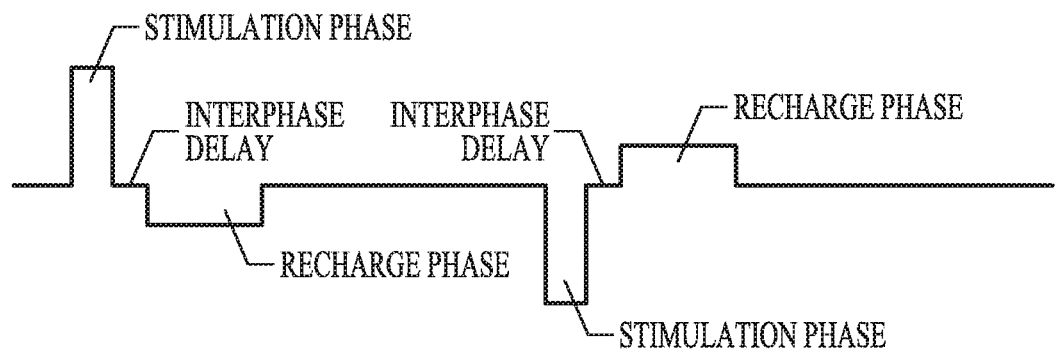
Figure 12H:
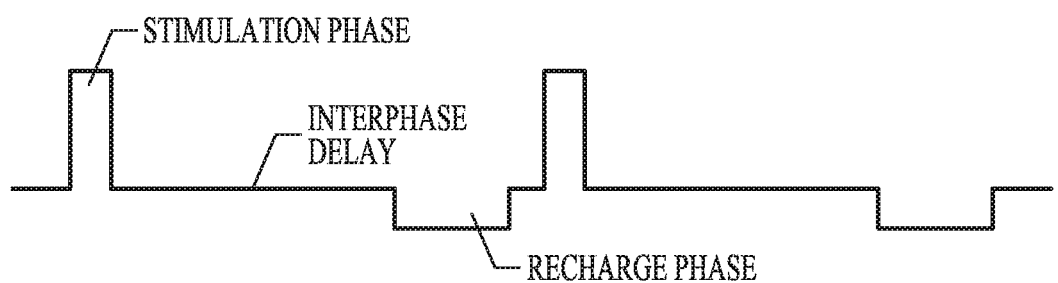
Figure 12I:
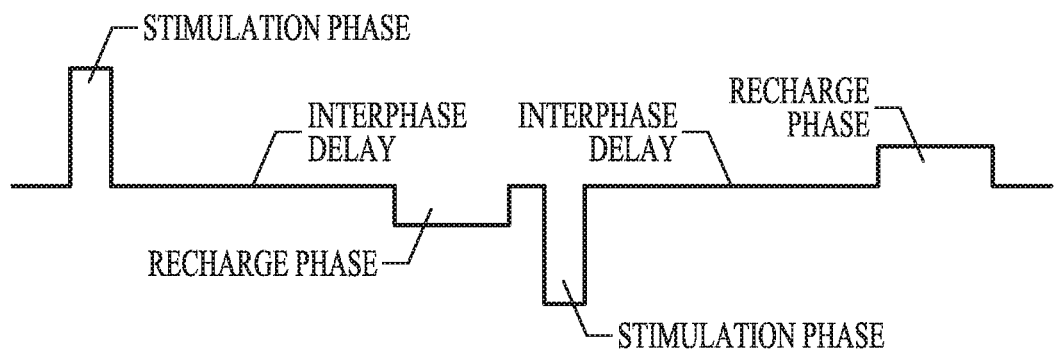

FIG. 12A illustrates am example of a passive recharge waveform with the stimulation phase being a square-wave pulse. FIGS. 12B-D each illustrate an example of an active recharge waveform with the stimulation phase and the recharge phase having symmetric pulse shapes. FIG. 12B illustrates an example of the active recharge waveform with the stimulation phase and the recharge phase each being a square-wave pulse. FIG. 12C illustrates an example of the active recharge waveform with the stimulation phase and the recharge phase each being a sine-wave pulse. FIG. 12D illustrates an example of the active recharge waveform with the stimulation phase and the recharge phase each being a triangular-wave pulse. FIGS. 12E-I each illustrate an example of an active recharge waveform with the stimulation phase and the recharge phase having asymmetric pulse shapes. FIG. 12E illustrates an example of the active recharge waveform with an anodic stimulation phase and a cathodic recharge phase being rectangular-wave pulses having different amplitudes. FIG. 12F illustrates an example of the active recharge waveform with a cathodic stimulation phase and an anodic recharge phase being rectangular-wave pulses having different amplitudes. FIG. 12G illustrates an example of the active recharge waveform with the stimulation phase and the recharge phase having alternating polarities (e.g., an anodic stimulation phase with a cathodic recharge phase, followed by a cathodic stimulation phase with an anodic recharge phase, and repeating) while being rectangular-wave pulses having different amplitudes. FIG. 12H illustrates an example of the active recharge waveform with an anodic stimulation phase and a cathodic recharge phase being rectangular-wave pulses having different amplitudes and a long interphase delay (i.e., the waveform of FIG. 12E with a longer interphase delay). FIG. 12I illustrates an example of the active recharge waveform with a long interphase delay and the stimulation phase and the recharge phase having alternating polarities while being rectangular-wave pulses having different amplitudes delay (i.e., the waveform of FIG. 12G with a longer interphase delay). These waveforms are shown by way of example for illustrative purposes, and not by way of limitation. For example, each waveform as illustrated in FIGS. 12A-I can have revered polarities, and the various polarities and pulse shapes can be combined, depending on the neurostimulation pattern as designed by those skilled in the art.

The stimulation parameters can also include one or more fields each specifying a spatial distribution of the neurostimulation energy across the plurality of electrodes. In one embodiment, each field is specified by one or more active electrodes selected from the plurality of electrodes. In another embodiment, each field is specified by fractionalization of a current flowing through each electrode of the plurality of electrodes.

In various embodiments, selecting the neurostimulation therapy pattern from the plurality of neurostimulation test patters can include, for example, selecting a therapy parameter from a plurality of test parameters or selecting a therapy set of parameters from a plurality of test sets of parameters. For example, selecting the neurostimulation therapy pattern from the plurality of neurostimulation test patters can include, for example, selecting a therapy waveform from a plurality of test waveforms and/or selecting a therapy field from a plurality of test fields.

Referring back to FIG. 11, Stimulation control circuit 1160 can include a sensing input 1162, a measurement circuit 1164, a selection circuit 1166, and an adjustment circuit 1168. Sensing input 1162, measurement circuit 1164, and selection circuit 1166 can represent an example of sensing input 962, measurement circuit 964, and selection circuit 966, respectively.

Sensing input 1162 can receive an ESG signal from ESG sensor 1174. The ESG signal is indicative of responses evoked by the neurostimulation energy delivered from stimulation output circuit. In various embodiments, sensor 1174 can sense one or more ESG signals to be received by sensing input 1162, depending on the need for obtaining information sufficient for selecting the neurostimulation therapy pattern.

Measurement circuit 1164 can determine one or more neural response parameters using the ESG signal received by sensing input 1162. The one or more neural response parameters are each indicative of one or more characteristics of the evoked responses. The one or more neural response parameters each have values corresponding to the plurality of neurostimulation test patterns. These values each correspond to a test pattern of the plurality of neurostimulation test patterns.

Selection circuit 1166 can select a neurostimulation therapy pattern from the plurality of stimulation test patterns for controlling the delivery of the neurostimulation energy based on the one or more neural response parameters and one or more selection criteria. In one embodiment, selection circuit 1166 selects a neurostimulation therapy pattern based on one neural response parameter. The neural response parameter has a plurality of values corresponding to the plurality of neurostimulation patterns. The neurostimulation therapy pattern to be selected is the test pattern corresponding to an optimal value of the plurality of values. In another embodiment, selection circuit 1166 selects a neurostimulation therapy pattern based on multiple neural response parameters (e.g., a parameter metric). The multiple neural response parameters have a plurality of sets of values corresponding to the plurality of neurostimulation test patterns. The neurostimulation therapy pattern to be selected is the test pattern corresponding to an optimal set of values of the plurality sets of values. The one or more selection criteria define the optimal value or the optimal set of values. Examples of the optimal value or the optimal set of values include a value or set of values:

(a) that maximizes or minimizes overall dorsal column (DC) response;

(b) that maximizes or minimizes response of specific DC fibers (e.g., myelinated DC fibers, unmyelinated DC fibers, $A\beta$ fibers, $A\delta$ fibers, and fast or slow fibers); and (c) that maximizes the response of a group of fibers while minimizing the response of another group of fibers (e.g., that maximizes response of $A\beta$ fibers while minimizing response of $A\delta$ fibers response, or that maximizes response of fast fibers while minimizing response of slow fibers).

These responses of different DC fiber types can be determined by extracting features of ECAP from the ESG signal. Examples of such features include:

area under the curve (e.g., area under the curve for different time windows, involving different relevant ECAP peaks in the ESG signal that correlate with faster or slow fibers)

curve length or relative curve length, where the relative curve length refers to measuring the curve length on two different time windows and comparing these two measured curve lengths by subtraction or division, where the first time window includes P2 and the second window includes P3 (it is noted that the relative curve length can be defined over time windows on any portion of the ESG signal, for example a first time window spanning from the start of a stimulus until 0.4 ms, and a second time window spanning from 0.8 ms until 2.2 ms, where the curve lengths of these time windows may correspond to the curve length of the stimulation artifact, and the curve length of the N1 to P2 response, respectively);

N1-to-P2 amplitude or other peak-to-peak amplitudes each specified for two peaks;

P2 peak delay;

Morphological changes; and curve length of the derivative (slope) of the ESG signal.

The one or more neural response parameters can include any one or any combination of these features (e.g., any linear or non-linear mathematical combination of any two or more of these features). Any of these features (neural response parameters) can be determined for any particular time window. An example of using the morphological changes as the features includes using wavelets to detect or recognize specific signal shape. A known ECAP response, or its changes or ceasation, can be detected using a wavelet. Mulitple "wavelet" templates corresponding to different shape morphologies of the neural response can be stored to allow for detection of changes (e.g., becoming thinner or wider) in the neural response using a wavelet, among other ways.

If the process for each selection of the neurostimulation therapy pattern takes time $t_{min}$, after making a selection, selection circuit 1166 can make the next selection (e.g., update the selection) after $t_{min}$ has passed. If the selection is to be made by selection circuit periodically at a period $t_i$, $t_i$ must be longer than $t_{min}$ (i.e., $t_i > t_{min}$). In other words, selection circuit 1166 can update the selection at a frequency $f_i$ ($f_i = 1/t_i$), which must be lower than $1/t_{min}$. In one embodiment, selection circuit 1166 makes an initial selection of the neurostimulation therapy pattern, and no update at a periodic basis or following another predetermined schedule is needed. In another embodiment, selection circuit 1166 updates the selection only when such a need arises, such as when the user changes the stimulation field (e.g., by activating different electrodes or modifying the fractionalization). In another embodiment, selection circuit 1166 checks the selection frequently, such as periodically or by following a schedule, and updates the selection in response to such a need being identified by the checking. One reason is that the spinal cord is surrounded by the cerebrospinal fluid (CSF). The CSF acts as a cushion to protect the spinal cord from breaking during physical movements of the body. The spinal cord moves softly and freely inside the CSF contained within the dura, which is a bag-like membrane structure that holds the CFS together surrounding the spinal cord. During physical movements of the body, the spinal cord moves in a 3-dimensional space. Consequently, the locations of the electrodes (e.g., epidural electrodes) relative to the spinal cord change. The electrodes are normally stabilized within fat tissue in the epidural space. As the spinal cord moves, its distance to each of the electrodes changes, leading to changes in the sensed ESG. Such changes can include changes in both the neural and non-neural components of the ESG. Selection circuit 1166 can be set to compensate for such changes by checking and updating the selection of the neurostimulation therapy pattern at a desirable frequency, such as a frequency that is empirically determined. This frequency can be set at a value that is less than $1/t_{min}$.

Following the selection of the neurostimulation therapy pattern, stimulation control circuit 1160 can control the delivery of the neurostimulation energy from stimulation output circuit 1170 according to the selected neurostimulation therapy pattern. System 1100 can include an adjustment circuit 1168 to adjust one or more stimulation parameters of the selected neurostimulation therapy pattern based on the one or more neural response parameters measured after the delivery of the neurostimulation energy according to the neurostimulation therapy pattern has started. In various embodiments, adjustment circuit 1168 can adjust the one or more stimulation parameters of the selected neurostimulation therapy pattern so that a value of each of the adjusted one or more stimulation parameters is maintained within a specified range.

In various embodiments, ESG sensor 1174 senses, and sensing input 1162 receives, the ESG signal, and measurement circuit 1164 determines one or more neural response signals (which can be the same as, or different from, the one or more neural response signals determined for the selection of the neurostimulation therapy pattern) while the neurostimulation energy is delivered according to the neurostimulation therapy pattern. Adjustment circuit 1168 adjusts the one or more stimulation parameters to automatically preserve the activation of the various DC fibers by increasing or decreasing the intensity of stimulation and or by steering the stimulation field to a direction that preserves the activation. In various embodiments, adjustment circuit 1168 can preserve an optimized neural response by adjusting the one or more stimulation parameter to, for example:

limit the changes of the neural signal morphology within a specified tolerance range;

limit the changes of the N1-to-P2 amplitude within a specified tolerance range;

limit the changes of the P2-to-N2 amplitude within a specified tolerance range;

limit the changes of the N1-to-P2 curve length within a specified tolerance range;

limit the changes of the P2-to-N2 curve length within a specified tolerance range;

limit the changes of the area under the curve for each of the peaks in the evoked response within a specified tolerance range;

limit the changes of the delay of P2 and the delay of N2 each within a specified tolerance range; and/or limit the changes of the ESG curve length, range, or area under the curve within specified time windows (e.g., 0.5 ms to 3 ms, as measured from a reference time such as the start of each stimulus).

Examples of the stimulation parameters that can be adjusted by adjustment circuit 1168 to preserve the optimized neural response can include any one of any combination of amplitude (e.g., current amplitude), pulse width, frequency, interphase delay, duration of the stimulation phase (while preserving charge balance), duration of the recharge phase (while preserving charge balance), cycling on-duration, and cycling-off duration.

Figure 13:
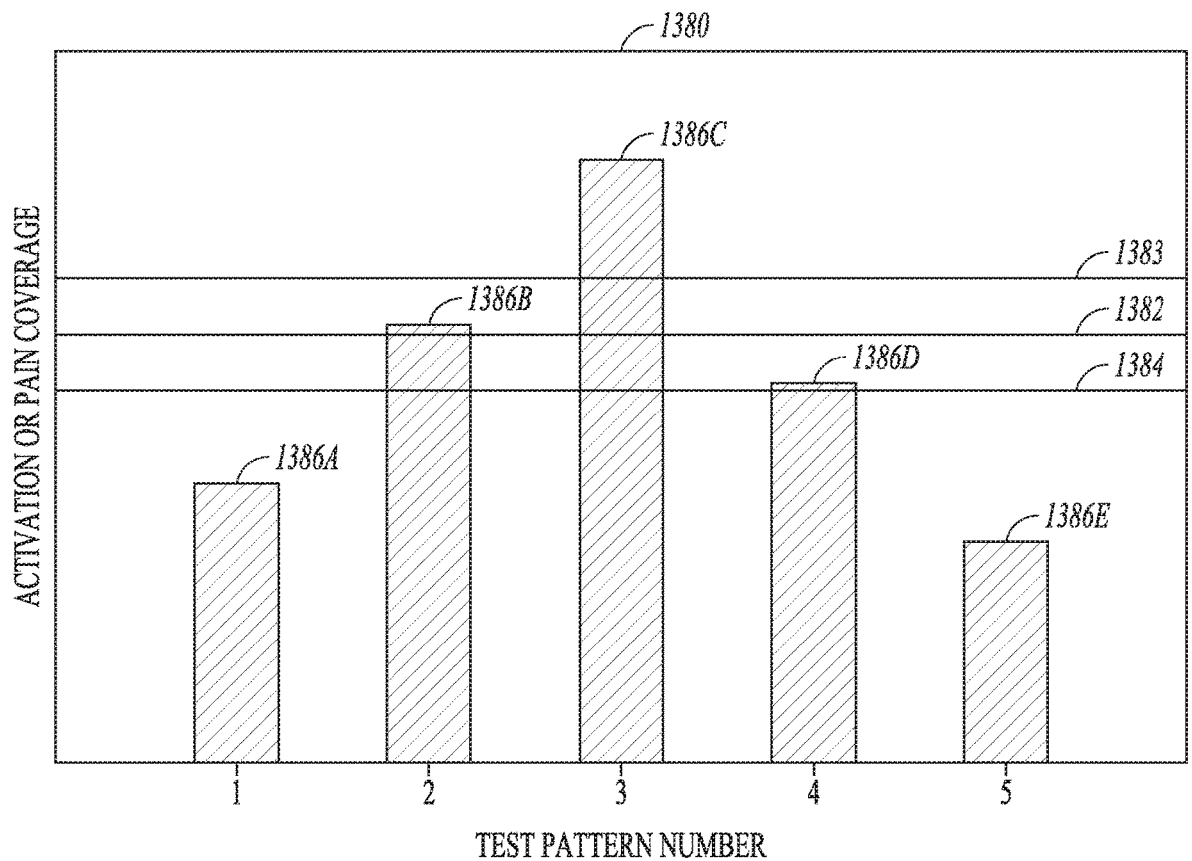
FIG. 13 illustrates an embodiment of a display screen area allowing a user to select a neurostimulation pattern using ESG.

FIG. 13 illustrates an embodiment of a display screen area 1380 allowing the user to select a neurostimulation pattern using ESG. Display screen area 1380 can be a portion of a display screen (e.g., a window) of a user interface, such as presentation device 856 of user interface 810. The user interface also includes a user input device, such as user input device 858. In an embodiment in which the user can manually select the neurostimulation therapy pattern from the plurality of neurostimulation test patterns, the user input device is used to receive the selection from the user.

Selection circuit 1166 can cause the measured values or sets of values of the one or more neural response parameters for the plurality of neurostimulation test patterns and/or their representation to be displayed in display screen area 1380. In various embodiments, selection circuit 1166 can also cause instructions guiding the user to select the neurostimulation therapy pattern based on the displayed information to be displayed in display screen area 1380. In the illustrated embodiment, bars 1386A-E each representing an amount of activation (e.g., magnitude of the DC response) or pain-paresthesia overlap resulting from delivering the neurostimulation energy according to one of several (5 illustrated by way of example and not by way of restriction) neurostimulation test patterns. The height of each of bars 1386A-E are determined based on the measured value or set of values of the one or more neural response parameters for one of the neurostimulation test patterns. Selection circuit 1166 can further cause an optimal value and/or an optimal or suitable range for the amount of activation or pain coverage to be displayed in display screen area 1380. In the illustrated embodiment, selection circuit 1166 causes display of an optimal value (height) 1382 and an optimal or suitable range defined by an upper threshold 1383 and a lower threshold 1384. With the example of various heights of bars 1386A-E shown in FIG. 13, the user may select test pattern number 2 to be the neurostimulation therapy pattern because the corresponding bar 1386B has a height closest to optimal value 1382, or may select test pattern number 4 for a compelling reason (e.g., substantially lower stimulation intensity of power consumption) because the corresponding bar 1386D has a height with the optimal or suitable range, while test patterns numbers 1, 3, and 5 are not to be selected because their corresponding bars 1386A, C, and E are outside of the optimal or suitable range.

The illustrated embodiment can be used with various selection criteria such as the criterion of selection based on maximum evoked response and the criterion of selection based on maximum pain-paresthesia overlap as discussed above. The height of each of bars 1386A-E (i.e., amount of activation or pain coverage) can quantitatively indicate the magnitude of the evoked response (e.g., DC response) or degree of similarity (e.g., a correlation coefficient) with a previously recorded ESG signal known for maximizing the pain-paresthesia overlap. It is noted that the optimal or suitable range may be defined by a single threshold (e.g., lower threshold 1384, when optimal means maximum without a specified upper limit).

Figure 14:
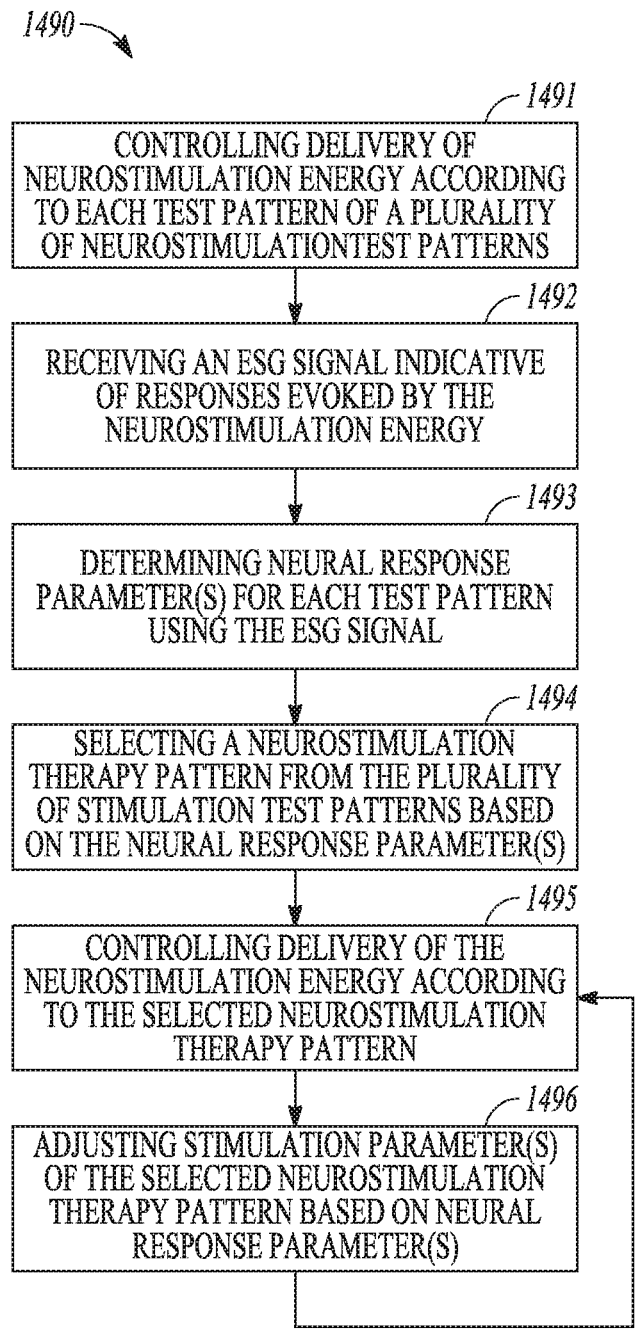
FIG. 14 illustrates an embodiment of a method for delivering neurostimulation including selecting a neurostimulation pattern using ESG.

FIG. 14 illustrates an embodiment of a method 1490 for delivering neurostimulation including selecting a neurostimulation pattern using ESG. In one embodiment, method 1490 is performed using system 1100, with stimulation control circuit 1160 configured (e.g., programmed) to perform the selection of neurostimulation pattern according to the present subject matter. Method 1400 can be performed to select a neurostimulation therapy pattern from a plurality of neurostimulation test patterns. In various embodiments, the selection can include selecting a waveform specifying a temporal pattern of the neuromodulation energy and/or selecting a field specifying a spatial distribution of the neurostimulation energy across the plurality of electrodes. The waveform can be an active recharge waveform or a passive recharge waveform.

At 1491, delivery of the neurostimulation energy is controlled according to each test pattern of a plurality of neurostimulation test patterns. At 1492, an ESG signal is received. In various embodiment, the ESG signal can be sensed epidurally using one or more electrodes placed over the spinal cord and/or intradurally using one or more electrodes placed within (at least partially) the spinal cord. The ECG signal is indicative of responses evoked by the delivered neurostimulation energy. At 1493, one or more neural response parameters for each test pattern of the plurality of neurostimulation test patterns are determined using the received ESG signal. The one or more neural response parameters are each indicative of one or more characteristics of the evoked responses. While method 1490 relates to selection of a neurostimulation therapy pattern based on the one or more neural parameters as an example, the present subject matter can also be applied to select the neurostimulation therapy pattern based on other parameters derivable from measurements of the ESG.

At 1494, a neurostimulation therapy pattern is selected from the plurality of stimulation test patterns based on the one or more neural response parameters and one or more selection criteria. In various embodiments, the selection can be made automatically, manually, or automatically but with input from the user. In various embodiments, the determination at 1493 can include determining values of the one or more neural response parameters each corresponding to a test pattern of the plurality of neurostimulation test patterns, and the selection at 1494 can include selecting the test pattern corresponding to a value of the determined values identified according to the one or more selection criteria. According to one example of a selection criterion, the test pattern corresponding to a maximum evoked response identified from the evoked responses corresponding to the plurality of neurostimulation test patterns is to be selected at 1494. For identifying the maximum evoked response, the one or more neural response parameters to be determined at 1493 can include at least one of a curve area being an area between the ESG signal and a baseline over a specified time interval, a curve length being a duration of the evoked responses over a specified time interval, a peak-to-peak amplitude being a difference between amplitudes of two specified-type peaks in the ESG signal or one or more neural response parameters measured from a derivative of the received ESG signal. According to one example of another selection criterion, the test pattern corresponding to a maximum pain-paresthesia overlap identified from the evoked responses corresponding to the plurality of neurostimulation test patterns is to be selected. In various embodiments, the one or more selection criteria used for selecting the neurostimulation therapy pattern can include either or both of these two criteria, any one or more other suitable criteria, or any combination of these two and other criteria. In one embodiment, the selection of the neurostimulation therapy pattern from the plurality of stimulation test patterns includes selecting a type of stimulation waveform from multiple types of stimulation waveform in the plurality of stimulation test patterns. For example, the plurality of stimulation test patterns can include multiple types of stimulation waveform (e.g., active recharge waveforms with different waveform shapes), and the neurostimulation therapy pattern corresponds to the most suitable type of stimulation waveform identified according to the one or more selection criteria.

At 1495, the delivery of the neurostimulation energy is controlled according to the selected neurostimulation therapy pattern. At 1496, one or more stimulation parameters of the selected neurostimulation therapy pattern are adjusted based on the one or more neural response parameters measured after the delivery of the neurostimulation energy according to the neurostimulation therapy pattern has started. This adjustment is to maintain a value of each of the adjusted one or more stimulation parameters within a specified range during the delivery of the neurostimulation energy according to the neurostimulation therapy pattern, such that the evoked response obtained with the selected neurostimulation therapy pattern can be preserved throughout the therapy. In various embodiments, steps 1491-1494 can be repeated when the evoked response obtained with the selected neurostimulation therapy pattern can no longer be preserved by adjusting the one or more stimulation parameters. This can be done, for example, by checking the performance of the current selection periodically and/or updating the selection when such a need is detected.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation energy through a plurality of electrodes to a patient having a spinal cord, the system comprising:
   a stimulation control circuit configured to control the delivery of the neurostimulation energy according to each test pattern of a plurality of neurostimulation test patterns including stimulation waveforms each specifying a temporal pattern of the neuromodulation energy including a waveform type selected from multiple waveform types including various recharge waveforms, the stimulation control circuit including:
   a sensing input configured to receive an electrospinogram (ESG) signal recording electrical activity from the spinal cord, the electrical activity including responses to the delivered neurostimulation energy;
   a measurement circuit configured to determine one or more response parameters for each test pattern of the plurality of neurostimulation test patterns using the received ESG signal, the one or more response parameters each indicative of one or more characteristics of the responses to the delivered neurostimulation energy; and
   a selection circuit configured to select a neurostimulation therapy pattern from the plurality of neurostimulation test patterns based on the one or more response parameters and one or more selection criteria, the selection including selecting the waveform type from the multiple waveform types in the plurality of neurostimulation test patterns.

2. The system of claim 1, wherein the measurement circuit is configured to determine one or more neural response parameters of the one or more response parameters, the one or more neural response parameters each indicative of one or more characteristics of evoked responses each being a neural response evoked by the delivered neurostimulation energy, and the selection circuit is configured to select the neurostimulation therapy pattern from the plurality of neurostimulation test patterns based on the one or more neural response parameters and the one or more selection criteria.

3. The system of claim 1, wherein the neurostimulation test patterns are each defined by one or more waveforms of the stimulation waveforms, and the multiple waveform types comprise active recharge waveforms.

4. The system of claim 3, wherein the neurostimulation test patterns are each further defined by one or more fields each specifying a spatial distribution of the neurostimulation energy across the plurality of electrodes.

5. The system of claim 4, wherein the selection circuit is configured to select the neurostimulation therapy pattern by selecting the test pattern corresponding to a maximum pain-paresthesia overlap identified from the evoked responses corresponding to the plurality of neurostimulation test patterns.

6. The system of claim 1, wherein the measurement circuit is further configured to determine values of the one or more neural response parameters each corresponding to a test pattern of the plurality of neurostimulation test patterns, and the selection circuit is further configured to select the neurostimulation therapy pattern by selecting the test pattern corresponding to a value of the determined values that indicates a maximum evoked response of the evoked responses corresponding to the plurality of neurostimulation test patterns.

7. The system of claim 6, wherein the measurement circuit is further configured to determine at least one of:
   a curve area of the one or more neural response parameters, the curve area being an area between the ESG signal and a baseline over a specified time interval;
   a curve length of the one or more neural response parameters, the curve length being a duration of the evoked responses over a specified time interval; or
   a peak-to-peak amplitude of the one or more neural response parameters, the peak-to-peak amplitude being a difference between amplitudes of two specified-type peaks in the ESG signal.

8. The system of claim 6, wherein the measurement circuit is further configured to produce a derivative of the received ESG signal and further configured to determine one or more additional neural response parameters using the produced derivative of the received ESG signal, the one or more additional neural response parameters each indicative of one or more further characteristics of the evoked responses.

9. The system of claim 1, wherein the stimulation control circuit is further configured to control the delivery of the neurostimulation energy according to the selected neurostimulation therapy pattern and further comprises a adjustment circuit configured to adjust one or more stimulation parameters of the selected neurostimulation therapy pattern based on the one or more neural response parameters measured after the delivery of the neurostimulation energy according to the neurostimulation therapy pattern has started.

10. The system of claim 9, wherein the adjustment circuit is further configured to adjust the one or more stimulation parameters of the selected neurostimulation therapy pattern so that a value of each of the adjusted one or more stimulation parameters is maintained within a specified range.

11. A method for delivering neurostimulation energy through a plurality of electrodes to a patient having a spinal cord, the method comprising:
controlling delivery of the neurostimulation energy according to each test pattern of a plurality of neurostimulation test patterns including stimulation waveforms each specifying a temporal pattern of the neuromodulation energy including a waveform type selected from multiple waveform types including various recharge waveforms;
receiving an electrospinogram (ESG) being a recording of electrical activity from the spinal cord, the electrical activity including responses to the delivered neurostimulation energy;
determining one or more response parameters for each test pattern of the plurality of neurostimulation test patterns using the received ESG signal, the one or more response parameters each indicative of one or more characteristics of the responses to the delivered neurostimulation energy; and
selecting a neurostimulation therapy pattern from the plurality of neurostimulation test patterns based on the one or more response parameters and one or more selection criteria, including selecting a waveform type from the multiple waveform types in the plurality of neurostimulation test patterns.

12. The method of claim 11, wherein determining the one or more response parameters comprises determining one or more neural response parameters each indicative of one or more characteristics of evoked responses each being a neural response evoked by the delivered neurostimulation energy, and selecting the neurostimulation therapy pattern comprises selecting the neurostimulation therapy pattern from the plurality of neurostimulation test patterns based on the one or more neural response parameters and the one or more selection criteria.

13. The method of claim 12, wherein the multiple waveform types comprise active recharge waveforms.

14. The method of claim 12, wherein selecting the neurostimulation therapy pattern further comprises selecting a field specifying a spatial distribution of the neurostimulation energy across the plurality of electrodes.

15. The method of claim 12, wherein determining the one or more neural response parameters comprises determining values of the one or more neural response parameters each corresponding to a test pattern of the plurality of neurostimulation test patterns, and selecting the neurostimulation therapy pattern comprises selecting the test pattern corresponding to a value of the determined values that indicates a maximum evoked response of the evoked responses corresponding to the plurality of neurostimulation test patterns.

16. The method of claim 15, wherein determining the one or more neural response parameters comprises determining at least one of:
a curve area being an area between the ESG signal and a baseline over a specified time interval;
a curve length being a duration of the evoked responses over a specified time interval;
a peak-to-peak amplitude being a difference between amplitudes of two specified-type peaks in the ESG signal; or
one or more neural response parameters measured from a derivative of the received ESG signal.

17. The method of claim 15, wherein selecting the neurostimulation therapy pattern comprises selecting the test pattern corresponding to a maximum pain-paresthesia overlap identified from the evoked responses corresponding to the plurality of neurostimulation test patterns.

18. The method of claim 11, further comprising:
controlling the delivery of the neurostimulation energy according to the selected neurostimulation therapy pattern; and
adjusting one or more stimulation parameters of the selected neurostimulation therapy pattern based on the one or more neural response parameters measured after the delivery of the neurostimulation energy according to the neurostimulation therapy pattern has started so that a value of each of the adjusted one or more stimulation parameters is maintained within a specified range during the delivery of the neurostimulation energy according to the neurostimulation therapy pattern.

19. A non-transitory computer-readable storage medium including instructions, which when executed by a system, cause the system to perform a method for delivering neurostimulation energy through a plurality of electrodes to a patient having a spinal cord, the method comprising:
controlling delivery of the neurostimulation energy according to each test pattern of a plurality of neurostimulation test patterns including stimulation waveforms each specifying a temporal pattern of the neuromodulation energy including a waveform type selected from multiple waveform types including various recharge waveforms;
receiving an electrospinogram (ESG) being a recording of electrical activity in the spinal cord, the electrical activity including responses to the delivered neurostimulation energy;
determining one or more response parameters for each test pattern of the plurality of neurostimulation test patterns using the received ESG signal, the one or more response parameters each indicative of one or more characteristics of the responses to the delivered neurostimulation energy; and
selecting a neurostimulation therapy pattern from the plurality of neurostimulation test patterns based on the one or more response parameters and one or more selection criteria, including selecting a waveform type from the multiple waveform types in the plurality of neurostimulation test patterns.

20. The non-transitory computer-readable storage medium of claim 19, wherein determining the one or more response parameters comprises determining one or more neural response parameters each indicative of one or more characteristics of evoked responses each being a neural response evoked by the delivered neurostimulation energy, and selecting the neurostimulation therapy pattern comprises selecting the neurostimulation therapy pattern from the plurality of neurostimulation test patterns based on the one or more neural response parameters and the one or more selection criteria.

\* \* \* \* \*